United States Patent [19]

Kissel et al.

[11] 4,215,147

[45] * Jul. 29, 1980

[54] ACROLEIN COMPOSITION AND METHOD OF ENHANCING EFFECTIVE LIFE THEREOF IN AN AQUEOUS MEDIUM

[75] Inventors: Charles L. Kissel, Anaheim; Frederick F. Caserio, Jr., Laguna Beach, both of Calif.

[73] Assignee: Magna Corporation, Santa Fe Springs, Calif.

[*] Notice: The portion of the term of this patent subsequent to Jul. 29, 1997, has been disclaimed.

[21] Appl. No.: 916,417

[22] Filed: Jun. 16, 1978

[51] Int. Cl.² ............................................. A01N 9/24
[52] U.S. Cl. ...................................... 424/333; 71/66; 71/77
[58] Field of Search ........................................ 424/333

[56] References Cited

U.S. PATENT DOCUMENTS

| | | | |
|---|---|---|---|
| 2,925,315 | 2/1960 | Pasternak | 424/333 |
| 3,250,667 | 5/1966 | Legator | 424/333 |

OTHER PUBLICATIONS

Chemical Abstracts, vol. 84 (1976), p. 63478s.

*Primary Examiner*—Leonard Schenkman
*Attorney, Agent, or Firm*—William C. Norvell, Jr.

[57] ABSTRACT

The life of acrolein in an aqueous medium is increased by incorporation into the aqueous medium of an effective amount of an acid preferably selected from the class consisting of: (1) $H_xA_y$, wherein H is hydrogen, A is an inorganic radical, and x and y each are positive integers whereby H and A are valence balanced; (2) RA, wherein R is one of hydrogen, an alkyl or an aryl group, and A is one of $CO_2H$, $OPO_3H_2$, $PO_3H_2$, $OSO_3H$, and $SO_3H$; and (3)

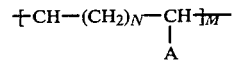

wherein N is zero or a positive integer from one through three, M is a positive integer of at least one, and A is a member selected from the class consisting of $CO_2H$, $OPO_3H_2$, $PO_3H_2$, $OSO_3H$, and $SO_3H$.

17 Claims, No Drawings

ACROLEIN COMPOSITION AND METHOD OF ENHANCING EFFECTIVE LIFE THEREOF IN AN AQUEOUS MEDIUM

CROSS REFERENCE TO RELATED APPLICATION

This application is related in subject matter to copending application Ser. No. 916,418, filed on even date herewith, and entitled "Acrolein Buffering Composition and Method of Enhancing Effective Life of Acrolein in an Aqueous Medium", Charles L. Kissel and Fredrick R. Caserio, Jr., Inventors, and assigned to the same assignee as this application.

BACKGROUND OF THE INVENTION

1. FIELD OF THE INVENTION

The invention relates to an acrolein composition and method of enhancing the lifetime of acrolein in an aqueous medium by incorporation of an organic or inorganic acid, or combinations thereof, to the aqueous medium and thereby adjusting the pH of the medium of from between about 2 and about 6.

2. DESCRIPTION OF THE PRIOR ART

Acrolein is used in numerous fresh water environments, as well as in brines and salt water, to kill aerobic, anaerobic, and sulfate-reducing bacteria, to remove aquatic weeds and snails, and to destroy algae, fungi, and other undesirable aquatic organisms. Of particular importance is the special use of acrolein in oilfield brines because of its potential biocidal action. This use of acrolein increases the efficiency of oilfield waterflooding and brine disposal operations. Acrolein also is used in oil field operations to scavenge deadly hydrogen sulfide. As the lifetime of acrolein is increased, the number of undesirable organisms destroyed increases, as does the amount of hydrogen sulfide scavenged.

Heretofore, it has been thought that the rate of the decline in acrolein concentration in an aqueous medium will inherently increase as the acid concentration increases and the pH decreases. This rate of decline in acrolein concentration has been reported to conform to the Hammett acidity function. Even the containers bearing commercial acrolein generally carry warning labels recommending that it be kept away from all acids, and particularly, strong acids, such as hydrochloric acid and sulfuric acid.

Acrolein inherently declines in concentration in aqueous medium. The period of time between the initial acrolein injection and that time at which the acrolein becomes ineffective as either a biocide, herbicide, or hydrogen sulfide scavenger, is defined as the acrolein lifetime.

It has been found that variables such as temperature and composition of phases present in the aqueous based medium will cause both dilution and effective disappearance of acrolein. Since these aqueous environments generally flow, the acrolein will decline in concentration at considerable distance downstream from the injection point. Increasing the initial injection concentration of acrolein does not significantly alter the distance-time relationship at which the acrolein is depleted to an ineffective level.

One obvious solution involves the usage of multiple injection sites. However, this solution increases the cost of treatments involving acrolein in an arithmatic relationship to the number of injection sites. Additionally, since acrolein is a somewhat difficult material to handle, the multiple injection solution increases the danger of possible environmental accidents.

SUMMARY OF THE INVENTION

It has been discovered that, contrary to previously published statements and beliefs, surprisingly, the lifetime of acrolein can, in fact, be substantially increased by lowering the pH of the aqueous medium containing the acrolein from normal values from between about 7 to about 8, to a range of from between about 2 to about 6, with a preferred or optimum range from between about 3 and about 4. Regardless of the nature of the aqueous medium, the lifetime of acrolein may be increased by actually lowering the pH of the system. Lowering of the pH of the aqueous medium can be accomplished by the addition of an acid selected from the class consisting of: (1) $H_xA_y$, wherein H is hydrogen, A is an inorganic radical, and x and y each are positive integers whereby H and A are valence balanced; (2) RA, wherein R is one of hydrogen, an alkyl or an aryl group, and A is one of $CO_2H$, $OPO_3H_2$, $PO_3H_2$, $OSO_3H$, and $SO_3H$; and (3)

Table I

| Sulfuric Acid Addition | pH | Lifetime of Acrolein at 35° C. (in hours) |
|---|---|---|
| — | 7 | 5 |
| 0.05 ml. | 5.5 | 6 |
| 0.07 ml. | 4.5 | 10 |
| 0.077 ml. | 3.5 | 208 |
| 0.24 ml. | 2.1 | 131 |

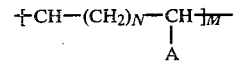

wherein N is zero or a positive integer from one through three, M is a positive integer of at least one, and A is a member selected from the class consisting of $CO_2H$, $OPO_3H_2$, $PO_3H_2$, $OSO_3H$, and $SO_3H$.

DESCRIPTION OF THE PREFERRED EMBODIMENTS

Lowering of the pH of an aqueous medium from about 7 to an acidic value between about 2 and about 6 has been found to substantially increase the lifetime of acrolein. It has been found that the maximum beneficial increase in the lifetime of acrolein is obtained when the pH of the aqueous medium is adjusted to from between about 3 and about 4. However, the exact pH necessary to obtain the optimum enhancement in the lifetime of acrolein is directly dependent upon the physical and chemical characteristics of the particular aqueous medium to be treated. Preferably, the lifetime of acrolein can be further increased at any given pH by using the anion of a strong acid, as opposed to using an anion of a weaker acid. Regardless of the choice of anion, the lifetime of acrolein will be increased at a lower or acidic pH when compared with an equivalent aqueous medium having a neutral pH.

Exemplary of some of the acids which may be utilized in the present invention are acetic acid, benzoic acid, formic acid, phosphoric acid, sulfuric acid, hydrochloric acid, sulfamic acid and nitric acid. The stronger acids, such as sulfuric acid, hydrochloric and acetic acid are preferred.

The pH of the aqueous medium may be adjusted to the acid side either prior to or after the desired amount of acrolein is introduced into the medium. Of course, the amount of acid necessary to adjust the aqueous medium to the desired pH level is dependent upon the strength of the selected acid, the composition of the aqueous medium itself, and the extension of effective life desired for the acrolein in the aqueous medium. Well known and commercially available techniques and equipment used in determining and monitoring pH levels may be utilized to determine when a sufficient and desired amount of acid material has been introduced into the aqueous medium.

The invention is further illustrated in the following examples:

EXAMPLE I

Ten ml. acrolein was introduced into 90 ml. of a 6% brine solution having dissolved solids therein as follows:
NaCl: 3.51%
$MgCl_2$: 1.59%
$Na_2SO_4$: 0.58%
$CaCl_2$: 0.17%
KCl: 0.10%
$NaHCO_3$: 0.03%
KBr: 0.01%
$H_3PO_3$: 0.01%
$SrCl_2$: 0.02%
NaF: 0.001%

The brine solution containing the acrolein was maintained at 35° C. while varying amounts of deuterated sulfuric acid were thereafter incrementally added to the aqueous medium. Since nuclear magnetic resonance was utilized to measure the extended acrolein lifetime, deuterium oxide also was utilized for tracing and monitoring purposes only. Nuclear magnetic resonance calculations were obtained by withdrawing 0.5 ml. aliquots of aqueous medium containing the acrolein and the incremental addition of acid and thereafter examining the nuclear magnetic resonance signal at 9.44 ppm. The area of the signal is a function of concentration and was compared to a tetramethylsilane sealed external standard. Graphs were plotted against time and acrolein lifetimes computed in accordance with each pH reading. The evaluation procedure is further described in Brady, et al, *Oil Field Subsurface Injection of Water*, A.S.T.M., S.T.P. 641, pp. 89-108 (1977).

The results of this test clearly indicated that the lifetime of acrolein in the 6% brine solution was significantly extended by the addition of sulfuric acid to reduce the pH. The results are further illustrated in the table below:

Table I

| Sulfuric Acid Addition | pH | Lifetime of Acrolein at 35° C. (in hours) |
| --- | --- | --- |
| — | 7 | 5 |
| 0.05 ml. | 5.5 | 6 |
| 0.07 ml. | 4.5 | 10 |
| 0.077 ml. | 3.5 | 208 |
| 0.24 ml. | 2.1 | 131 |

EXAMPLE II

Exactly 0.01 ml. acrolein was added to 99.99 ml. of a 6% solution of brine at 35° C. The brine contained the same dissolved solids in the percentages described in EXAMPLE I. The initial concentration of acrolein was 100 ppm. The method used to analyze the effective lifetime of acrolein was differential pulse polaragraphy using 10 ml. aliquots, with graphs being constructed by plotting concentration against time to obtain a lifetime computation. The differential pulse polarography technique is further detailed in Howe, *Analytical Chemistry*, Vol. 48, p. 2167 (1976).

The pH of the brine solutions containing the acrolein was adjusted by the addition of various acids, described in Tables II. It was found that all of the aqeuous brine media produced an enhanced lifetime for acrolein at reduced acidic pH's than would have been possible at neutral pH 7. This test clearly shows that acids composed of anions from strong acids increase the lifetime of acrolein somewhat more effectively than an aqueous medium containing acidic anions from weaker acids.

Table II

| Acid-Amount | pH | Lifetime of Acrolein at 35° C. (in hours) |
| --- | --- | --- |
| — | 7 | 5 |
| $HClO_4$ 0.075 Ml. | 4 | 140 |
| $H_2SO_4$ 0.073 ml. | 4 | 132 |
| $HNO_3$ 0.074 ml. | 4 | 115 |
| HCl 0.07 ml. | 4 | 108 |
| $C_2H_4O_3$ 0.71 ml. | 4 | 95 |
| $H_3PO_4$ 0.69 ml. | 4 | 91 |
| HOAC 0.75 ml. | 4 | 60 |
| Polyacrylic Acid 9.56 ml. (MW = 1,000) | 4 | 58 |

EXAMPLE III

The present example illustrates a field test of the invention. The location of the test was an oil field operation near Woodward, Oklahoma. The aqueous medium was analyzed and the composition found to be as follows:

| | | | |
| --- | --- | --- | --- |
| Ag | 0.5 ppm. | Na | 3500 ppm. |
| Ba | 20 ppm. | Sr | 50 ppm. |
| Ca | 95 ppm. | Zn | 0.3 ppm. |
| Cr | 0.5 ppm. | Cl | 9696 ppm. |
| Cu | 1 ppm. | $SO_4$ | 180 ppm. |
| Fe | 2 ppm. | $CO_3$ | 1461 ppm. |
| K | 1500 ppm. | $PO_4$ | 2 ppm. |
| Mg | 135 ppm. | Sulfide | 20 ppm. |
| Mo | 0.5 ppm. | pH | 7.4 ppm. |

Acrolein was utilized as a hydrogen sulfide scavenger. When 0.01 ml. acrolein was added to 99.99 ml. of this aqueous medium, the acrolein as measured by the polarograph technique was determined to be 90 minutes at 33° C., while the hydrogen sulfide level was reduced to only 10 ppm. When 99.98 ml. of the aqueous medium was reacted with 0.01 ml. of 98% sulfuric acid and thereafter mixed with 0.01 ml acrolein, the acrolein lifetime became 4 days at pH 3.5 at 33° C., which reduced the hydrogen sulfide to 1 ppm.

Although the invention has been described in terms of specified embodiments which are set forth in detail, it should be understood that this is by way of illustration only and that the invention is not necessarily limited thereto, since alternative embodiments and operating techniques will become apparent to those skilled in the art in view of the disclosure. Accordingly, modifications are contemplated which can be made without departing from the spirit of the described invention.

What is claimed and desired to be secured by Letters Patent is:

1. A method of enhancing the effective life of acrolein in an aqueous medium, comprising the steps of: (A) introducing into said aqueous medium a predeterminable amount of acrolein; and (B) adjusting the pH of the aqueous medium having acrolein present therein to from between about pH 6 and about pH 2.

2. A method of enhancing the effective life of acrolein in an aqueous medium, comprising the steps of: (A) adjusting the pH of the aqueous medium having acrolein present therein to from between about pH 6 and about pH 2; and (B) introducing into said aqueous medium a predeterminable amount of acrolein.

3. A method of enhancing the effective life of acrolein in an aqueous medium comprising the steps of: (A) introducing into said aqueous medium a predeterminable amount of acrolein; and (B) adjusting the pH of the aqueous medium having acrolein present therein by contacting said medium with an effective pH-reducing amount of an acid solution, whereby said aqueous medium having acrolein present therein is reduced to from between about ph 6 and pH 2.

4. A method of enhancing the effective life of acrolein in an aqueous medium comprising the steps of: (A) adjusting the pH of the aqueous medium by contacting said medium with an effective pH-reducing amount of an acid solution, whereby said aqueous medium is reduced to from between about pH 6 and about pH 2; and (B) introducing into said acidic aqueous medium a predeterminable amount of acrolein.

5. A method of enhancing the effective life of acrolein in an aqueous medium comprising the steps of: (A) introducing into said aqueous medium a predetermined amount of acrolein; and (B) adjusting the pH of the aqueous medium having acrolein present therein by contacting said medium with an effective pH-reducing amount of an acid selected from the class consisting of: (1) $H_xA_y$, wherein H is a hydrogen, A is an inorganic radical, and x and y each are positive integers whereby H and A are valence balanced; (2) RA, wherein R is one of hydrogen, an alkyl or an aryl group, and A is one of $CO_2H$, $OPO_3H_2$, $PO_3H_2$, $OSO_3H$, and $SO_3H$; and (3)

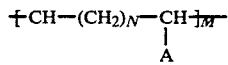

wherein N is zero or a positive integer from one through three, M is a positive integer of at least one, and A is a member selected from the class consisting of $CO_2H$, $OPO_3H_2$, $PO_3H_2$, $OSO_3H$, and $SO_3H$.

6. The method of claim 5 wherein said acid is hydrochloric acid.

7. The method of claim 5 wherein said acid is sulfuric acid.

8. The method of claim 5 wherein said acid is acetic acid.

9. A method of enhancing the effective life of acrolein in an aqueous medium comprising the steps of: (A) adjusting the pH of the aqueous medium having acrolein present therein by contacting said medium with an effective pH-reducing amount of an acid selected from the class consisting of: (1) $H_xA_y$, wherein H is hydrogen, A is an inorganic radical, and x and y each are positive integers whereby H and A are valence balanced; (2) RA, wherein R is one of hydrogen, an alkyl or an aryl group, and A is one of $CO_2H$, $OPO_3H_2$, $PO_3H_2$, $OSO_3H$, and $SO_3H$; and (3)

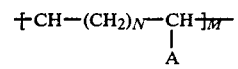

wherein N is zero or a positive integer from one through three, M is a positive integer of at least one, and A is a member selected from the class consisting of $CO_2H$, $OPO_3H_2$, $PO_3H_2$, $OSO_3H$, and $SO_3H$; and (B) introducing into said aqueous medium a predetermined amount of acrolein.

10. The method of claim 9 wherein said acid is hydrochloric acid.

11. The method of claim 9 wherein said acid is sulfuric acid.

12. The method of claim 9 wherein said acid is acetic acid.

13. A method of enhancing the effective life of acrolein in an aqueous medium comprising the steps of: (A) introducing into said aqueous medium a predetermined amount of acrolein; and (B) adjusting the pH of the aqueous medium having acrolein present therein by contacting said medium with an effective pH-reducing amount of an acid selected from the class consisting of: (1) $H_xA_y$, wherein H is hydrogen, A is an inorganic radical, and x and y each are positive integers whereby H and A are valence balanced; (2) RA, wherein R is one of hydrogen, an alkyl or an aryl group, and A is one of $CO_2H$, $OPO_3H_2$, $PO_3H_2$, $OSO_3H$, and $SO_3H$; and (3)

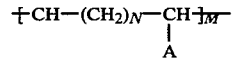

wherein N is a zero or a positive integer from one through three, M is a positive integer from at least one, and A is a member selected from the class consisting of $CO_2H$, $OPO_3H_2$, $PO_3H_2$, $OSO_3H$, and $SO_3H$, said pH thereby being adjusted and reduced to between about pH 6 and about pH 2.

14. A method of enhancing the effective life of acrolein in an aqueous medium comprising the steps of: (A) introducing into said aqueous medium a predetermined amount of acrolein; and (B) adjusting the pH of the aqueous medium having acrolein present therein by contacting said medium with an effective pH-reducing amount of an organic acid, an inorganic acid or mixtures thereof selected from the class consisting of: (1) $H_xA_y$, where H is hydrogen, A is an inorganic radical, and x and y each are positive integers whereby H and A are valence balanced; (2) RA, wherein R is one of hydrogen, and alkyl or an aryl group, and A is one of $CO_2H$, $OPO_3H_2$, $PO_3H_2$, $OSO_3H$, and $SO_3H$; and (3)

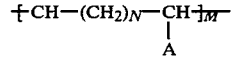

wherein N is zero or a positive integer from one through three, M is a positive integer of at least one, and A is a member selected from the class consisting of $CO_2H$, $OPO_3H_2$, $PO_3H_2$, $OSO_3H$, and $SO_3H$, said pH thereby being adjusted and reduced to between about pH 6 and about pH 2.

15. A method of effectively reducing aerobic, anaerobic or sulfate-reducing bacteria in an aqueous medium comprising the steps of: (A) introducing into said aqueous medium a predetermined amount of acrolein; (B)

adjusting the pH of the aqueous medium having acrolein present therein by contacting said medium with an effective pH-reducing amount of an organic acid, an inorganic acid or mixtures thereof selected from the class consisting of: (1) $H_xA_y$, wherein H is hydrogen, A is an inorganic radical, and x and y each are positive integers whereby H and A are valence balanced; (2) RA, wherein R is one of hydrogen, an alkyl or an aryl group, and A is one of $CO_2H$, $OPO_3H_2$, $PO_3H_2$, $OSO_3H$, and $SO_3H$; and (3)

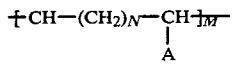

wherein N is zero or a positive integer from one through three, M is a positive integer of at least one, and A is a member selected from the class consisting of $CO_2H$, $OPO_3H_2$, $PO_3H_2$, $OSO_3H$, and $SO_3H$, said pH thereby being adjusted and reduced to between about pH 6 and about pH 2; and (C) contacting said aerobic, anaerobic or sulfate-reducing bacteria with an effective bacteria reducing amount of said acidic aqueous medium.

16. A method of effectively reducing aerobic, anaerobic or sulfate-reducing bacteria in an aqueous medium comprisng the steps of: (A) adjusting th pH of the aqueous medium by contacting said medium with an effective pH-reducing amount of an organic acid, an inorganic acid or mixtures thereof selected from the caass consisting of: (1) $H_xA_y$, wherein H is hydrogen, A is an inorganic radical, and x and y each are positive integers whereby H and A are valence balanced; (2) RA, wherein R is one of hydrogen, an alkyl or an aryl group, and A is one of $CO_2H$, $OPO_3H_2$, $PO_3H_2$, $OSO_3H$, and $SO_3H$; and (3)

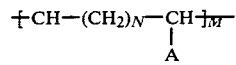

wherein N is zero or a positive integer from one through three, M is a positive integer of at least one, and A is a member selected from the class consisting of $CO_2H$, $OPO_3H_2$, $PO_3H_2$, $OSO_3H$, and $SO_3H$, said pH thereby being adjusted and reduced to between about pH 6 and about pH 2; (B) introducing into said aqueous medium a predetermined amount of acrolein; and (C) contacting said aerobic, anaerobic or sulfate-reducing bacteria with an effective bacteria reducing amount of said acidic aqueous medium.

17. A method of effectively rendering hydrogen sulfide inert in an aqueous medium comprising the steps of: (A) introducing into said aqueous medium a predetermined amount of acrolein; and (B) adjusting the pH of the aqueous medium having acrolein present therein by contacting said medium with an effective pH-reducing amount of an organic acid, an inorganic acid or mixtures thereof selected fromthe class consisting of: (1) $H_xA_y$, wherein H is hydrogen, A is an inorganic radical, and x and y each are positive integers whereby H and A are valence balanced; (2) RA, wherein R is one of hydrogen, an alkyl or an aryl group, and A is one of $CO_2H$, $OPO_3H_2$, $PO_3H_2$, $OSO_3H$, and $SO_3H$; and (3)

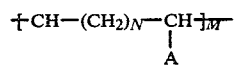

wherein N is zero or a positive integer from one through three, M is a positive integer or at least one, and A is a member selected from the class consisting of $CO_2H$, $OPO_3H_2$, $PO_3H_2$, $OSO_3H$, and $SO_3H$, said pH thereby being adjusted and reduced to between about pH 6 and about pH 2; and (C) contacting said hydrogen sulfide with said acidic aqueous medium.

* * * * *